(12) United States Patent
Varner et al.

(10) Patent No.: US 11,426,217 B2
(45) Date of Patent: Aug. 30, 2022

(54) PLANTAR BONE FUSION PLATE

(71) Applicant: IN2BONES USA, LLC, Memphis, TN (US)

(72) Inventors: Kevin E. Varner, Memphis, TN (US); Keith A. Heier, Memphis, TN (US); Travis W. Hanson, Memphis, TN (US); Casey M. Chambers, Memphis, TN (US); Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 208 days.

(21) Appl. No.: 15/611,528

(22) Filed: Jun. 1, 2017

(65) Prior Publication Data

US 2017/0348031 A1 Dec. 7, 2017

Related U.S. Application Data

(60) Provisional application No. 62/344,830, filed on Jun. 2, 2016.

(51) Int. Cl.
 *A61B 17/80* (2006.01)
(52) U.S. Cl.
 CPC ...... *A61B 17/8061* (2013.01); *A61B 17/8014* (2013.01); *A61B 17/8052* (2013.01)
(58) Field of Classification Search
 CPC ...... A61F 2/4225; A61F 2/4241; A61B 17/80; A61B 17/8052; A61B 17/8057
 USPC .......................... 623/21.15, 21.19; 606/289
 See application file for complete search history.

(56) References Cited

U.S. PATENT DOCUMENTS

| | | | |
|---|---|---|---|
| 6,890,335 B2 | 5/2005 | Grabowski et al. | |
| 2006/0241607 A1* | 10/2006 | Myerson | A61B 17/8061 606/280 |
| 2006/0241608 A1* | 10/2006 | Myerson | A61B 17/8061 606/280 |
| 2007/0016205 A1* | 1/2007 | Beutter | A61B 17/7291 623/17.11 |

(Continued)

OTHER PUBLICATIONS

International Search Report from Patent Application No. PCT/US2017/035527 dated Aug. 7, 2017.

*Primary Examiner* — David W Bates
(74) *Attorney, Agent, or Firm* — Rutan & Tucker LLP; Hani Z. Sayed

(57) ABSTRACT

A plantar bone plate and a method are provided for treating fractures of metatarsal bones. The plantar bone plate comprises a generally elongate member having an upper surface and a lower, bone contact surface. Two or more fixation apertures and a compression slot are disposed along a longitudinal dimension of the elongate member. The fixation apertures receive fasteners suitable for fastening the plantar bone plate to a metatarsal bone. The compression slot receives a fastener at an oblique angle for compressing adjacent portions of the metatarsal bone so as to encourage bone fusion. A curvature along the elongate member is configured to mate the plantar bone plate with the anatomy of the plantar aspect of the metatarsal bone. In one embodiment, the curvature is comprised of at least a first bend and a second bend, such that the plantar bone plate mates with the plantar anatomy of the $5^{th}$ metatarsal.

6 Claims, 4 Drawing Sheets

(56) References Cited

U.S. PATENT DOCUMENTS

| | | | | |
|---|---|---|---|---|
| 2007/0233114 A1* | 10/2007 | Bouman | A61B 17/80 | 606/280 |
| 2008/0015590 A1* | 1/2008 | Sanders | A61B 17/80 | 606/86 A |
| 2009/0093849 A1* | 4/2009 | Grabowski | A61B 17/8061 | 606/280 |
| 2009/0210013 A1* | 8/2009 | Kay | A61B 17/8014 | 606/286 |
| 2009/0275991 A1* | 11/2009 | Medoff | A61B 17/1775 | 606/297 |
| 2009/0306724 A1* | 12/2009 | Leither | A61B 17/8057 | 606/289 |
| 2010/0274293 A1* | 10/2010 | Terrill | A61B 17/8057 | 606/286 |
| 2011/0009866 A1* | 1/2011 | Johnson | A61B 17/1728 | 606/70 |
| 2011/0224737 A1* | 9/2011 | Lewis | A61B 17/1728 | 606/290 |
| 2012/0010617 A1* | 1/2012 | Ramos Maza | A61B 17/1746 | 606/70 |
| 2012/0209334 A1* | 8/2012 | Lewis | A61B 17/8014 | 606/286 |
| 2013/0172942 A1* | 7/2013 | Lewis | A61B 17/8014 | 606/281 |
| 2014/0066996 A1* | 3/2014 | Price | A61B 17/1728 | 606/281 |
| 2014/0180343 A1* | 6/2014 | Gaudin | A61B 17/8061 | 606/283 |
| 2014/0277176 A1* | 9/2014 | Buchanan | A61B 17/8061 | 606/281 |
| 2015/0142064 A1* | 5/2015 | Perez | A61B 17/8085 | 606/284 |
| 2016/0256204 A1* | 9/2016 | Patel | A61B 17/8014 | |
| 2017/0360488 A1* | 12/2017 | Kowalczyk | A61B 17/809 | |

* cited by examiner

PLANTAR BONE FUSION PLATE

PRIORITY

This application claims the benefit of and priority to U.S. Provisional Application, entitled "Plantar Bone Fusion Plate," filed on Jun. 2, 2016 and having application Ser. No. 62/344,830.

FIELD

The field of the present disclosure generally relates to securing bones together. More particularly, the field of the present disclosure relates to an apparatus and a method for fusing and compressing bones of the human body.

BACKGROUND

A fusion bone plate implant may be utilized in conjunction with one or more fasteners so as to generate compression and stability at a bone interface. An implant coupled with fasteners generally serves to stabilize bones, or bone parts, relative to one another so as to promote bone fusion. In many applications, bone plates and fasteners are used to fuse bones, or bone parts, of the human body, such as bones in the foot, the ankle, the hand, the wrist, as well as various other portions of the body. Furthermore, during the course of certain medical procedures, a surgeon may immobilize one or more bones or the bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

A plantar bone plate and a method are provided for treating fractures of metatarsal bones. The plantar bone plate comprises a generally elongate member having an upper surface and a lower, bone contact surface. Two or more fixation apertures and a compression slot are disposed along a longitudinal dimension of the elongate member. The two or more fixation apertures are configured to receive fasteners suitable for fastening the plantar bone plate to a metatarsal bone. The compression slot is configured to receive a fastener at an oblique angle for compressing adjacent portions of the metatarsal bone so as to encourage bone fusion. A curvature along the elongate member is configured to mate the plantar bone plate with the anatomy of the plantar aspect of the metatarsal bone. In one embodiment, the curvature is comprised of at least a first bend and a second bend such that the plantar bone plate mates with the plantar anatomy of the $5^{th}$ metatarsal. In some embodiments, the curvature is comprised of a combination of one or more curves along the longitudinal dimension and a lateral dimension of the plantar bone plate.

In an exemplary embodiment, a plantar bone plate for treating fractures of a metatarsal bone comprises a generally elongate member having an upper surface and a lower, bone contact surface; two or more fixation apertures disposed along a longitudinal dimension of the elongate member and configured to receive fasteners suitable for fastening the plantar bone plate to the metatarsal bone; a compression slot configured to receive a fastener perpendicular to the upper surface or at an oblique angle for compressing adjacent portions of the metatarsal bone so as to encourage bone fusion; and a curvature along the elongate member configured to mate with the anatomy of the plantar aspect of the metatarsal bone.

In another exemplary embodiment, the plantar bone plate is comprised of a material possessing a tensile strength suitable for immobilizing adjacent bone portions of the metatarsal bone. In another exemplary embodiment, the two or more fixation apertures are configured to receive bone screws. In another exemplary embodiment, the two or more fixation apertures comprises at least four fixation apertures. In another exemplary embodiment, the two or more fixation apertures each is comprised of a countersunk surface disposed below the upper surface and configured to allow a countersunk head of a fastener to assume a level that is above, flush with, or disposed below the upper surface when the fastener is tightened to hold the plantar bone plate against the metatarsal bone. In another exemplary embodiment, the countersunk surface comprises a chamfer angle of that ranges between substantially 60° and 120°. In another exemplary embodiment, the countersunk surface is configured to provide a locking feature that prevents the fastener from backing out after being implanted into a bone.

In another exemplary embodiment, the curvature is comprised of a first bend and a second bend along the longitudinal dimension of the plantar bone plate. In another exemplary embodiment, the first bend is comprised of a slightly curved portion that is concaved toward the upper surface and extends from substantially a middle portion of the plantar bone plate to a beginning of the second bend. In another exemplary embodiment, the second bend is comprised of a curved portion that is concaved away from the upper surface and extends from the first bend to a proximal end of the plantar bone plate. In another exemplary embodiment, a flat portion of the plantar bone plate extends from the first bend to a distal end of the plantar bone plate. In another exemplary embodiment, the first bend and the second bend comprise a tangent reverse curve. In another exemplary embodiment, the second bend comprises a smaller radius than a radius of the first bend. In another exemplary embodiment, the first bend and the second bend are configured so as to mate the plantar bone plate with the plantar anatomy of the metatarsal bone. In another exemplary embodiment, the first bend and the second bend are configured such that the curvature of the plantar bone plate mates with the plantar anatomy of the $5^{th}$ metatarsal.

In another exemplary embodiment, the curvature is comprised of one or more curves along a lateral dimension that is substantially perpendicular to the longitudinal dimension of the plantar bone plate. In another exemplary embodiment, the curvature is comprised of a combination of one or more curves along the longitudinal dimension and a lateral dimension of the elongate member. In another exemplary embodiment, the curvature is configured to mate the plantar bone plate with a specific anatomy of a bone to be treated.

In an exemplary embodiment, a method for a plantar bone plate for treating fractures of a metatarsal bone comprises providing a generally elongate member having an upper surface and a lower surface; disposing two or more fixation apertures along a longitudinal dimension of the elongate member; configuring the two or more fixation apertures to receive fasteners suitable for fastening the plantar bone plate to the metatarsal bone; forming a compression slot to receive a fastener perpendicular to the upper surface or at an oblique angle suitable for compressing adjacent portions of the metatarsal bone so as to encourage bone fusion; and applying a curvature along the elongate member such that the plantar bone plate mates with the anatomy of the plantar aspect of the metatarsal bone. In another exemplary embodiment, applying the curvature comprises forming at least a first bend and a second bend along the elongate member such that the plantar bone plate mates with the plantar anatomy of the $5^{th}$ metatarsal. In another exemplary embodiment, applying the curvature comprises forming a combination of one or more curves along the longitudinal dimension and a lateral dimension of the plantar bone plate.

BRIEF DESCRIPTION OF THE DRAWINGS

The drawings refer to embodiments of the present disclosure in which.

Figure 1:
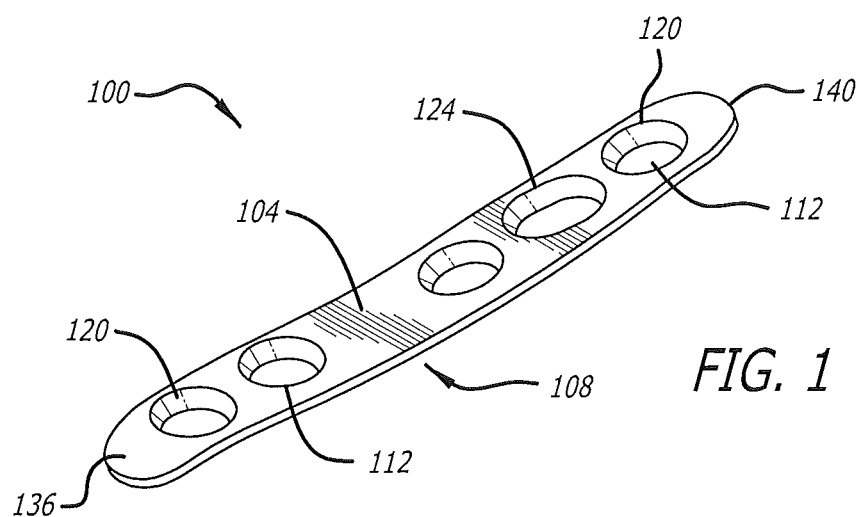
FIG. 1 illustrates an upper isometric view of an exemplary embodiment of a plantar bone plate for treating fractures of a metatarsal bone.
Figure 2:
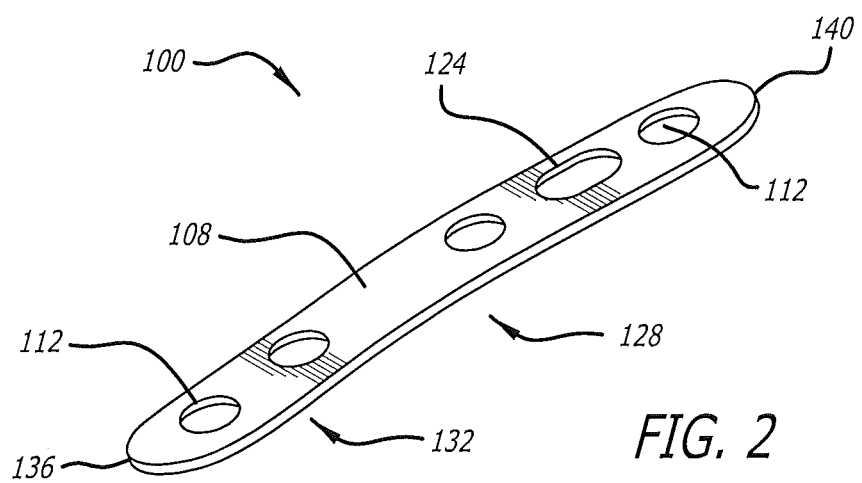
FIG. 2 illustrates a lower isometric view of the exemplary embodiment of the plantar bone plate illustrated in FIG. 1.
Figure 3:
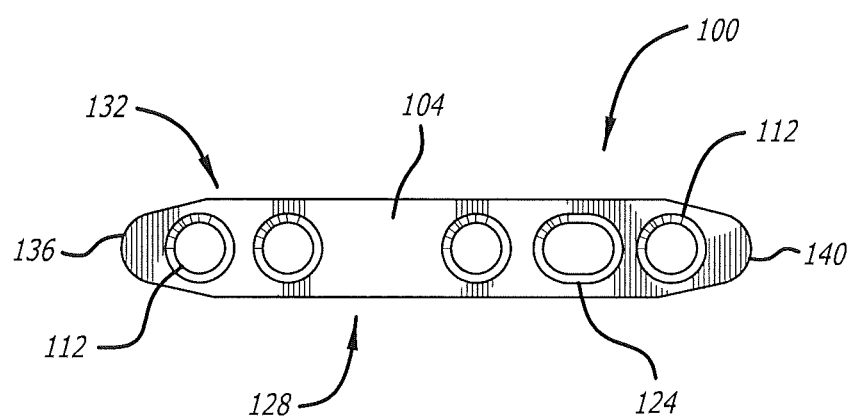
FIG. 3 illustrates a top plan view of the upper surface of the plantar bone plate illustrated in FIG. 1.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first screw," may be made. However, the specific numeric reference should not be interpreted as a literal sequential order but rather interpreted that the "first screw" is different than a "second screw." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and a method for a plantar bone plate for treating Jones fractures, Pseudo Jones fractures, and Avulsion fractures of the metatarsal bones. The plantar bone plate comprises a generally elongate member having an upper surface and a lower, bone contact surface. Two or more fixation apertures are disposed along a longitudinal dimension of the elongate member. The fixation apertures are configured to receive fasteners suitable for fastening the plantar bone plate to the a metatarsal bone. Each of the fixation apertures comprises a countersunk surface disposed below the upper surface of the plantar bone plate. The countersunk surface is configured to allow a countersunk head of the fastener to assume a level that is flush with, or disposed below, the upper surface when the fastener is tightened to hold the plantar bone plate against the metatarsal bone. A compression slot is configured to receive a fastener that is oriented at an oblique angle for compressing adjacent portions of the metatarsal bone so as to encourage bone fusion. A curvature along the elongate member is configured to match the anatomy of the plantar aspect of the metatarsal bone to be fused. In one embodiment, the curvature is comprised of at least a first bend and a second bend that are configured to mate the plant bone fusion plate with the anatomy of the plantar aspect of the $5^{th}$ metatarsal bone.

Figure 4:
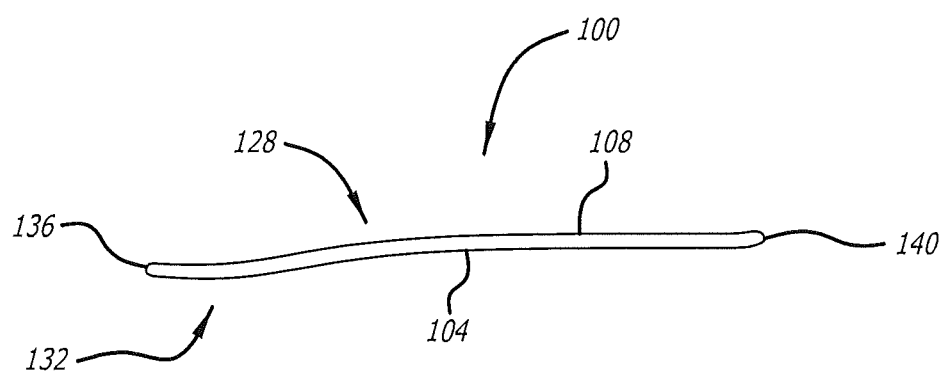
FIG. 4 illustrates a side profile view of a longitudinally-directed curvature of the plantar bone plate illustrated in FIG. 1.
Figure 5:
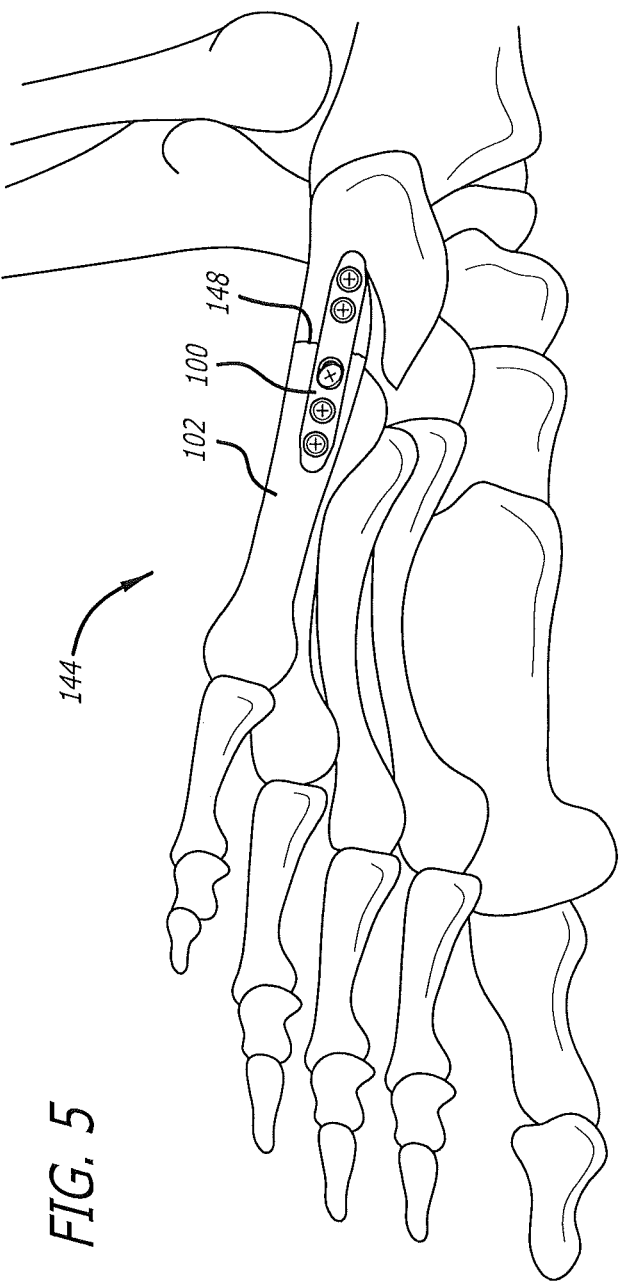
FIG. 5 illustrates an exemplary use environment wherein the plantar bone plate of FIG. 1 is fastened onto a plantar aspect of a $5^{th}$ metatarsal bone across a fracture site.
Figure 6:
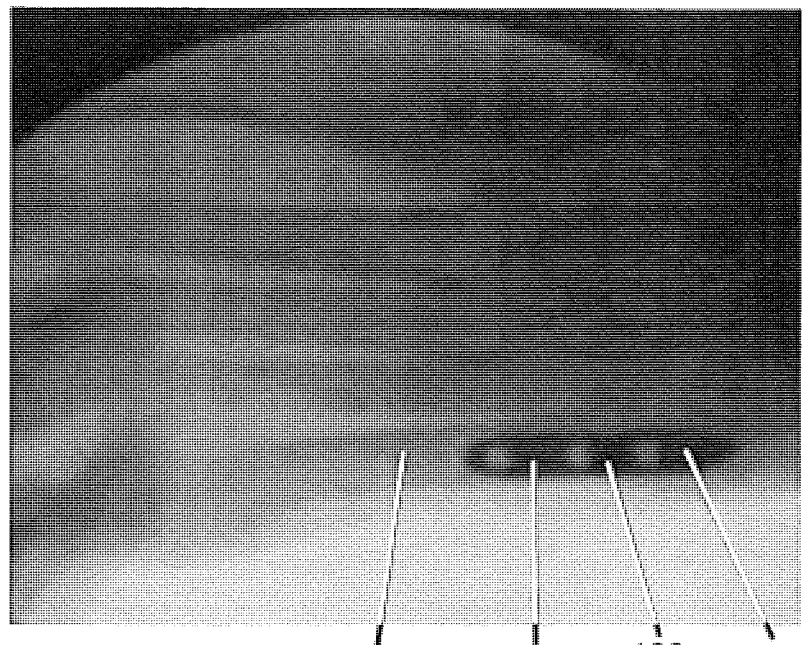
FIG. 6 illustrates a plan view of an exemplary use environment wherein the plantar bone plate of FIG. 1 has been implanted into a patient through a plantar lateral incision and fastened onto the $5^{th}$ metatarsal bone by way of two fasteners to treat a fracture.
Figure 7:
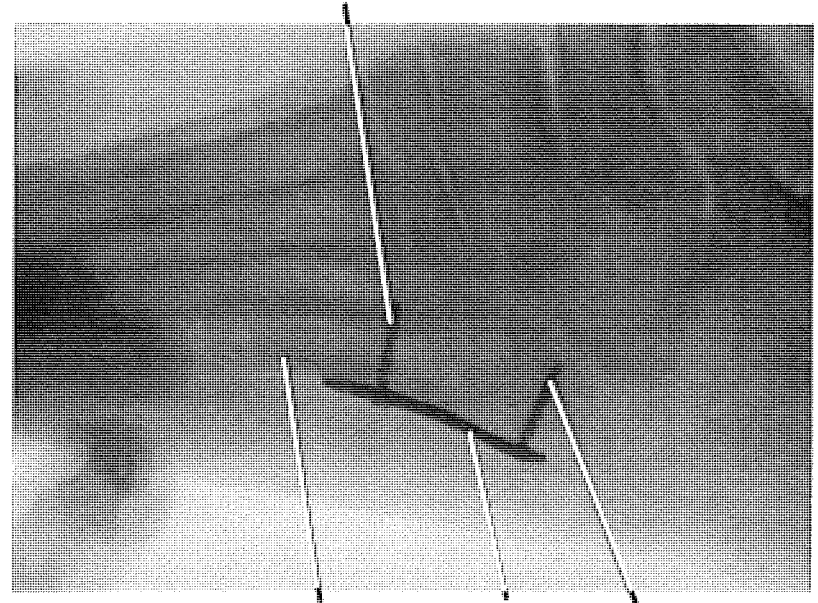
FIG. 7 illustrates a profile view of the exemplary use environment shown in FIG. 6.

FIGS. 1-5 illustrate an exemplary embodiment of a plantar bone plate 100 configured to treat Jones fractures, Pseudo Jones fractures, and Avulsion fractures of a $5^{th}$ metatarsal 102. Although the plantar bone plate 100 is shown in FIG. 5 to be fusing the $5^{th}$ metatarsal, it should be understood that the plantar bone plate may be adapted for treating fractures of any of the metatarsal bones, without limitation. The plantar bone plate 100 comprises a generally elongate member having an upper surface 104 and a lower, bone contact surface 108. Disposed along the plantar bone plate 100 are two or more fixation apertures 112 suitable for receiving fasteners 116, such as bone screws as shown in FIGS. 6-7. Preferably, the plantar bone plate 100 includes 4-5 fixation apertures 112, although in other embodiments the plantar bone plate may include less than 4 or more than 5 fixation apertures 112. The plantar bone plate 100 preferably is comprised of a semi-rigid material, such as a biocompatible metal or PEEK, possessing a tensile strength suitable for immobilizing adjacent bone portions of the $5^{th}$ metatarsal 102.

The fixation apertures 112 are configured to each receive a fastener 116, such as a bone screw that may be utilized to fasten the plantar bone plate 100 onto the $5^{th}$ metatarsal 102, as disclosed above and shown in FIGS. 5-7. Each fixation aperture 112 comprises a countersunk surface 120 disposed within the fixation aperture and below the upper surface 104 of the bone plate. As will be appreciated, the countersunk surface 120 allows a countersunk head of the fastener 116 to assume a level that is either above, flush with, or disposed below the upper surface 104 when the fastener is tightened to hold the plantar bone plate 100 against the bone. It is envisioned that the countersunk surfaces 120 may be implemented with any of various suitable chamfer angles, including, but not limited to, 60°, 82°, 90°, 100°, 110°, or 120°. In some embodiments, however, the chamfer angle of the countersunk surfaces 120 preferably is either 82° or 90°. Further, it is contemplated that the countersunk surfaces 120 comprise a locking feature that operates to prevent the fasteners 116 from backing out of the bone after having been implanted in a patient.

The plantar bone plate 100 preferably comprises at least one compression slot 124 configured to receive a fastener 116. Similar to the fixation apertures 112, the compression slot 124 may receive the fastener 116 at an angle of substantially 90° with respect to the plane of the plantar bone plate 100. Unlike the fixation apertures, however, the compression slot 124 may alternatively receive the fastener 116 at an oblique angle with respect to the plane of the plantar bone plate 100. The oblique angle of the fastener 116 facilitates compressing adjacent bone portions together so as to encourage bone fusion. The fastener 116 may be any component of hardware having a head configured to abut the surface of plantar bone plate 100 and a shaft configured to secure bone portions together in a fixed configuration. In some embodiments, the fastener 116 may comprise a lag screw which includes a head that is rounded, or tapered, and coupled to a shaft, or a shank, that has an unthreaded portion adjacent to the head and a threaded portion that ends at a tip.

As best illustrated in FIG. 4, a longitudinal dimension of the plantar bone plate 100 is comprised of a first bend 128 and a second bend 132. The first bend 128 is comprised of a smooth, slightly curved portion that is concaved toward the upper surface 104 and extending from substantially a middle portion of the plantar bone plate 100 to a beginning of the second bend 132. The second bend 132 is comprised of a curved portion concaved away from the upper surface 104 and extending from the first bend 128 to a proximal end 136 of the plantar bone plate 100. A relatively flat portion of the plantar bone plate 100 extends from the first bend 128 to a distal end 140 of the bone plate. In some embodiments, however, one or more curved portions may be incorporated into the portion of the plantar bone plate 100 between the first bend 128 and the distal end 140.

As shown in FIG. 4, the first bend 128 and the second bend 132 comprise a tangent reverse curve, wherein the second bend 132 comprises a relatively smaller radius than a radius of the first bend 128. As will be appreciated, the radius and concavity of the first bend 128, and the radius and concavity of the second bend 132 are selected such that the curvature of the plantar bone plate 100 substantially matches, or mates with, the plantar anatomy of the 5$^{th}$ metatarsal 102, as shown in FIG. 5. It is contemplated, however, that the radii and concavities of the first and second bends 128, 132 may be varied from those illustrated and disclosed herein, without limitation, so as to mate the plantar bone plate 100 to the anatomy of any of the metatarsal bones, as needed.

Moreover, it should be recognized that the plantar bone plate 100 is not to be limited to bends along the longitudinal dimension, but rather the plantar bone plate 100 may comprise a curvature along a lateral dimension of the plantar bone plate 100 that is substantially perpendicular to the longitudinal dimension, as well as a combination of curvatures along the longitudinal and lateral dimensions of the plantar bone plate. In some embodiments, the curvature may change along the longitudinal and lateral dimensions as a function of distance from a middle, or other reference location, of the plantar bone plate 100. In some embodiments, the curvatures along the longitudinal and lateral dimensions may be selected to match a specific anatomy of a bone to be treated other than the metatarsals. Accordingly, it should be understood that the plantar bone plate 100 may be implemented with any combination of topological features without deviating from the spirit and scope of the present disclosure.

FIG. 5 illustrates an exemplary use environment 144 wherein the plantar bone plate 100 is fastened onto the plantar aspect of the 5$^{th}$ metatarsal 102 across a bone fracture 148. It is contemplated that in practice, the plantar bone plate 100 may be implanted into the patient through a plantar lateral incision. For example, in an exemplary environment 152 illustrated in FIGS. 6-7, the plantar bone plate 100 has been implanted into a patient through a plantar lateral incision and fastened onto the 5$^{th}$ metatarsal 102 by way of two fasteners 116 to treat a fracture 148. As will be appreciated, with the plantar bone plate 100 fastened to the plantar aspect of the 5$^{th}$ metatarsal, the plantar bone plate is predominantly placed in tension under normal gait cycle loading, thereby naturally maintaining compression at the bone fracture 148. As such, it should be recognized that implanting the plantar bone plate 100 onto the plantar aspect of the 5$^{th}$ metatarsal is mechanically superior to placing the bone plate on a dorsal aspect of the bone. Further, it should be understood that the plantar bone plate 100 is not to be limited to treating fractures of the 5$^{th}$ metatarsal 102. Rather, it is contemplated that the plantar bone plate 100 may be adapted for treating various types of fractures to any of the metatarsal bones, as well as other bones of the human body, as needed.

It is envisioned that the embodiments discussed herein may be coupled with various surgical instruments that are configured for implanting the plantar bone plate 100 and fasteners 116 into patients. In some embodiments, the surgical instruments may include, without limitation, plate trials, wires, drills, drill guides, depth gages, cup and cone reamers, screw drivers, plate benders, and the like. It is further envisioned that the plantar bone plate 100, accompanying fasteners 116, and the selected surgical instruments are to be suitably sterilized for surgeries and packaged into sterilized containers. In some embodiments, the plantar bone plate 100 may be packaged into a first sterile container, the fasteners 116 may be packaged into a second sterile container, and the instruments may be packaged into a third sterile container. The first, second, and third sterile containers may then be bundled together into a single, exterior container, thereby forming a convenient surgery-specific bone fusion implant package. It is envisioned that other packaging techniques will be apparent to those skilled in the art without deviating from the spirit and scope of the present disclosure.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A plantar bone plate for treating fractures of a metatarsal bone, comprising:
   a generally elongate member having an upper surface and a lower, bone contact surface, the elongate member comprising a semi-rigid material;
   a curvature comprising a first bend and a second bend along the longitudinal dimension of the plantar bone plate;
   wherein the second bend comprises a smaller radius than a radius of the first bend, and wherein the radius and concavity of the first bend and the radius and concavity of the second bend are configured to mate with the anatomy of the plantar aspect of the metatarsal bone comprising a 5$^{th}$ metatarsal;

the first bend further comprising a curved portion extending from a middle portion of the plantar bone plate to a beginning of a second bend;

the second bend further comprising a curved portion concaved away from the upper surface and extending from the first bend to a proximal end of the plantar bone plate;

a plurality of fixation apertures disposed along a longitudinal dimension of the elongate member and configured to receive one or more fasteners;

wherein the plantar bone plate is comprised of a material possessing a tensile strength suitable for immobilizing adjacent bone portions of the metatarsal bone;

a compression slot configured to receive a fastener at a right angle or at an oblique angle with respect to a plane of the plantar bone plate to encourage bone fusion; and wherein the fastener has a head configured to abut a surface of the plantar bone plate and a shaft configured to secure bone portions together in a fixed configuration;

wherein each of the plurality of fixation apertures comprise a countersunk surface disposed within the fixation aperture and below the upper surface of the bone plate and configured to allow a countersunk head of the fastener to assume a level that is above, flush with, or disposed below the upper surface when the fastener is tightened to hold the plantar bone plate against the metatarsal bone;

wherein the countersunk surface comprises a chamfer angle that ranges between 82° and 120°, and a locking feature;

wherein the countersunk surface is configured to prevent the fastener from backing out after being implanted into the metatarsal bone; and wherein the curvature is configured to mate the plantar bone plate with a specific anatomy of a bone to be treated.

2. The bone plate of claim 1, wherein the two or more fixation apertures are configured to receive bone screws.

3. The bone plate of claim 1, wherein the two or more fixation apertures comprises at least four fixation apertures.

4. The bone plate of claim 1, wherein a flat portion of the plantar bone plate extends from the first bend to the distal end of the plantar bone plate.

5. The bone plate of claim 1, wherein the curvature is comprised of one or more curves along a lateral dimension of the plantar bone plate that is substantially perpendicular to the longitudinal dimension.

6. The bone plate of claim 1, wherein the curvature is comprised of a combination of one or more curves along the longitudinal dimension and a lateral dimension of the elongate member.

\* \* \* \* \*